(12) United States Patent
Wong

(10) Patent No.: US 6,627,152 B1
(45) Date of Patent: Sep. 30, 2003

(54) FLUID TESTING APPARATUS

(75) Inventor: Raphael C. Wong, Irvine, CA (US)

(73) Assignee: Branan Medical Corp., Irvine, CA (US)

( * ) Notice: Subject to any disclaimer, the term of this patent is extended or adjusted under 35 U.S.C. 154(b) by 64 days.

(21) Appl. No.: 09/620,347

(22) Filed: Jul. 20, 2000

Related U.S. Application Data

(60) Provisional application No. 60/200,683, filed on Apr. 29, 2000.

(51) Int. Cl.$^7$ ................................................. G01N 21/00
(52) U.S. Cl. ............................. 422/58; 422/55; 422/56; 422/57; 422/61; 422/68.1; 422/100; 422/102
(58) Field of Search .............................. 422/58, 56, 55, 422/57, 61, 68.1, 100, 102; 436/165, 178

(56) References Cited

U.S. PATENT DOCUMENTS

| | | |
|---|---|---|
| 3,774,455 A | 11/1973 | Seidler et al. |
| 3,924,741 A | 12/1975 | Kachur et al. |
| 4,024,952 A | 5/1977 | Leitz |
| 4,109,530 A | 8/1978 | Kim |
| 4,827,944 A | 5/1989 | Nugent |
| 5,119,830 A | 6/1992 | Davis |
| 5,215,102 A | 6/1993 | Guirguis |
| 5,403,551 A | 4/1995 | Galloway et al. |
| 5,501,837 A | 3/1996 | Sayles |
| 5,916,815 A | 6/1999 | Lappe |
| 5,976,895 A | 11/1999 | Cipkowski |
| 6,074,606 A * | 6/2000 | Sayles .......................... 422/58 |
| 6,168,758 B1 * | 1/2001 | Forsberg et al. ............... 422/61 |
| 6,342,183 B1 * | 1/2002 | Lappe et al. ................... 422/58 |

* cited by examiner

*Primary Examiner*—Jill Warden
*Assistant Examiner*—Sam P. Siefke
(74) *Attorney, Agent, or Firm*—Myers Dawes Andras & Sherman LLP; Vic Y. Lin

(57) ABSTRACT

A fluid testing apparatus comprises a vessel for collecting a fluid, a removable cap secured to the top of the vessel, and a movable carrier to transport a portion of the fluid in the vessel to test strips disposed within the cap. The test strips are disposed in cavities of the cap. One end portion of each test strip exits through an exit port on the bottom side of the cap. A rim on the bottom side of the cap surrounds the protruding end portions of the test strips. The movable carrier is movable between a retrieving position to collect the fluid and a testing position where the retrieved fluid is brought into contact with the protruding ends of the test strips. A spring bias mechanism causes the carrier to move toward the closed, testing position by default. In the testing position, the carrier's receptacle forms a seal with the surrounding rim and the bottom side of the cap to prevent the carried portion of the fluid from contacting the remaining, non-tested fluid in the vessel. A method for containing and testing a fluid is also provided.

18 Claims, 3 Drawing Sheets

FLUID TESTING APPARATUS

RELATED APPLICATIONS

This application relates to and claims priority from U.S. Provisional Application No. 60/200,683 entitled COMBINATION CONTAINER AND TEST DEVICE WITH A SCOOP filed on Apr. 29, 2000.

BACKGROUND OF THE INVENTION

1. Field of the Invention

The invention relates generally to chemical testing devices for fluids.

2. Description of Related Art

With the rise in demand for drug screening, an increasing need exists for an efficient, safe and cost effective way of testing fluids. The prior art includes cassettes which allow a tester to place drops of the fluid into wells. Using such a device, however, required the tester to transport urine from a container to the cassette, thus allowing for spillage and contact of the fluid.

Galloway et al., U.S. Pat. No. 5,403,551, discloses a cup with separate compartments which require the tester to tilt the cup in order to cause the fluid to move from one compartment to another. In Galloway, however, spillage can occur if the lid is not rotated to the precise position necessary to seal the cup.

The prior art also includes other cups with multiple compartments and different means of causing the fluid to move from one compartment to another, such as valves and rotatable walls. The complexity of such designs, however, lead to high costs in production and problems in operation.

SUMMARY OF THE INVENTION

A fluid testing apparatus comprises a container for containing a fluid, a movable carrier to carry at least a portion of the fluid, and a test strip disposed within the container to contact at least in part the portion of the fluid carried by the movable carrier. The container comprises a vessel and a cap. The test strip is disposed at least in part within the cap. The cap comprises a cavity disposed for receiving the test strip. The test strip is disposed at least in part within the cavity. The cap comprises a translucent material such that the test strip disposed within the cavity is viewable. The test strip comprises an end portion that projects downwardly from the cap so as to be accessible for contact with the fluid carried by the movable carrier. The cap further comprises a rim on a bottom side that surrounds the end portion of the test strip. The rim is adapted to form a sealing relationship with the movable carrier when the movable carrier is in a first, raised position. The cap is removably secured to the vessel. The movable carrier comprises a receptacle coupled to a bar. The receptacle is disposed beneath the cap and within the vessel. The bar extends through the cap. A bias mechanism is coupled to the cap to bias the carrier, including the receptacle, in an upward direction toward the test strip.

Alternatively stated, the fluid testing apparatus comprises a vessel to collect a fluid, a lid coupled to the vessel, a test strip disposed at least in part within the lid, and a movable carrier having a receptacle disposed within the vessel to carry a portion of the fluid. The movable carrier is movable between a retrieving position where the receptacle retrieves the portion of the fluid within the vessel and an testing position where the receptacle causes the portion of the fluid to come into contact with at least a portion of the test strip. The movable carrier forms a sealing relationship with the lid in the testing position. The testing position is an upper position and the retrieving position is a lower position. The apparatus further comprises a bias mechanism to bias the movable carrier toward the testing position. The lid is removable. The test strip comprises a drug test strip. Additional test strips may be provided with one of the strips being an adulteration strip disposed at least in part within the lid to test if the. liquid is contaminated.

In another aspect, a movable carrier is provided for transporting a fluid within a container that includes at least one test strip. The carrier comprises a receptacle and a bar coupled to the receptacle to enable movement of the receptacle. The receptacle is movable between a retrieving position for retrieving a portion of the fluid within the container and a testing position for causing the portion of the fluid to contact the test strip. The carrier further comprises a handle coupled to the bar. The receptacle comprises a bottom wall, a side wall, and a top opening.

A method is also provided for collecting and testing a fluid. The method comprises: collecting the fluid with a container; coupling a test strip to the container; carrying at least a portion of the fluid toward the test strip; and, contacting at least a portion of the test strip with the portion of the fluid. Carrying at least a portion of the fluid toward a test strip comprises: carrying the portion of the fluid with a carrier; and raising the carrier with the portion of the fluid toward the test strip. Carrying at least a portion of the fluid toward a test strip further comprises lowering the carrier to retrieve the portion of the fluid. The method further comprises preventing the carried portion of the fluid from contacting a remainder of the fluid in the container by sealing the carried portion of the fluid from a remainder of the fluid in the container. Contacting at least a portion of the test strip with the portion of the fluid comprises testing the portion of the fluid with the test strip. Collecting the fluid with a container comprises disposing the fluid into a vessel and coupling a lid to the vessel.

In conclusion, a fluid testing apparatus comprises a vessel for collecting a fluid, a removable cap secured to the top of the vessel, and a movable carrier to transport a portion of the fluid in the vessel to test strips disposed within the cap. The test strips are disposed in cavities of the cap. One end portion of each test strip exits through an exit port on the bottom side of the cap. A rim on the bottom side of the cap surrounds the protruding end portions of the test strips. The movable carrier is movable between a retrieving position to collect the fluid and a testing position where the retrieved fluid is brought into contact with the protruding ends of the test strips. A spring bias mechanism causes the carrier to move toward the closed, testing position by default. In the testing position, the carrier's receptacle forms a seal with the surrounding rim and the bottom side of the cap to prevent the carried portion of the fluid from contacting the remaining, non-tested fluid in the vessel. A method for containing and testing a fluid is also provided.

The invention, now having been briefly summarized, may be better visualized by turning to the following drawings wherein like elements are referenced by like numerals.

Figure 1:
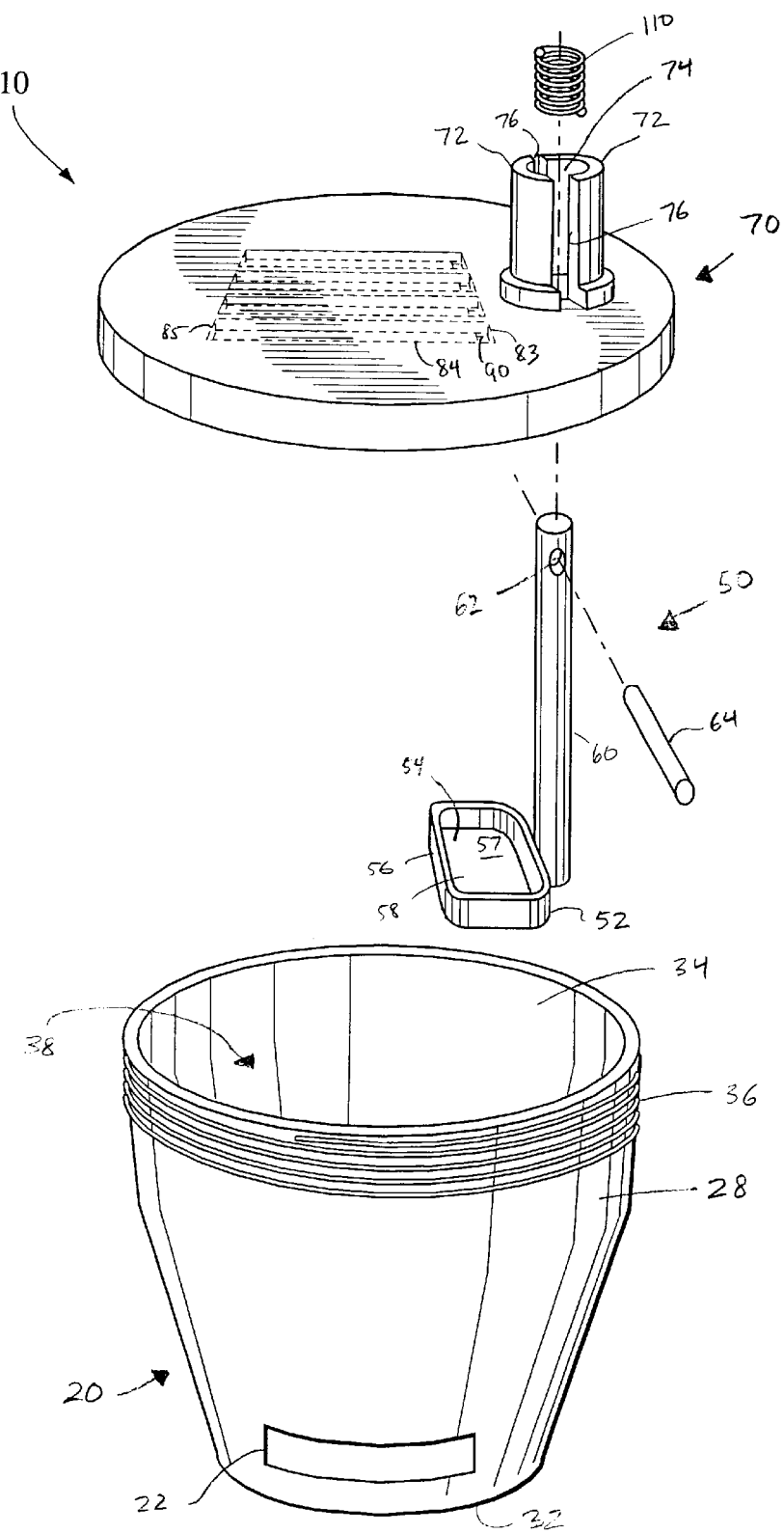
FIG. 1 is an exploded view of a fluid testing apparatus with test strips removed to more clearly illustrate the cavities in the cap.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS

A fluid testing apparatus according to the present invention is shown in the figures and designated generally by the reference numeral 10.

Figure 2:
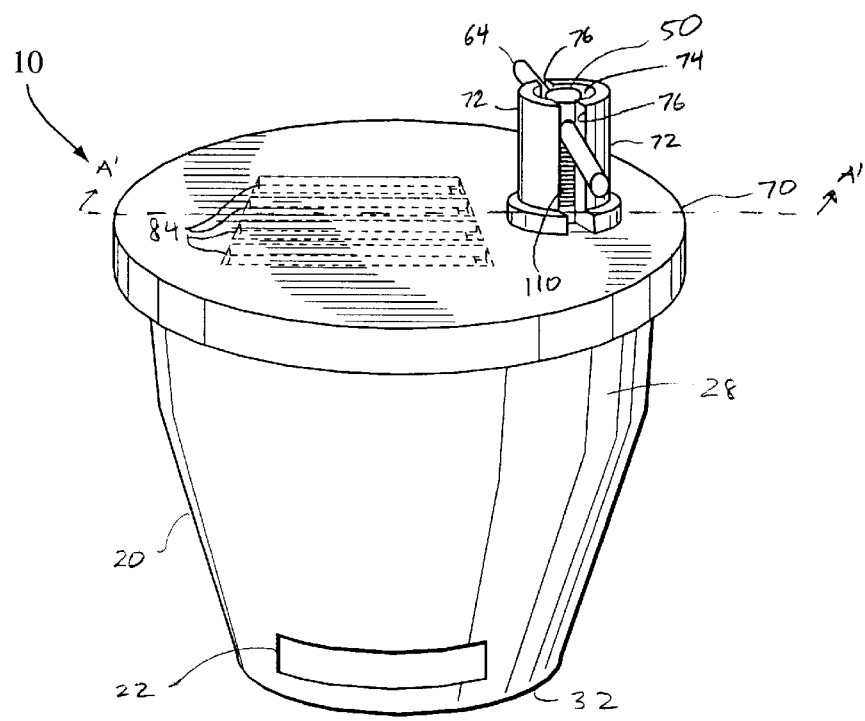
FIG. 2 is a perspective view of the fluid testing apparatus of FIG. 1.

FIGS. 1 and 2 are exploded and perspective views, respectively, of a fluid testing apparatus 10 with test strips removed to more clearly illustrate the structure of the cavities in the cap. The apparatus 10 comprises a vessel 20 for collecting fluid. Though the preferred function of the apparatus 10 is to test urine for the presence of illegal drugs, it is to be expressly understood that the apparatus 10 may test any type of fluid for the presence of any chemical. The vessel 20 comprises a temperature gauge 22 which measures the temperature of the fluid collected within the vessel 20. The temperature gauge 22 faces outwardly and enables a tester to view the measured temperature. The vessel comprises a bottom floor 32. Alternatively, the bottom floor 32 may be raised so as to require a lesser volume of urine to be collected in order for the apparatus 10 to operate. In FIG. 1, a top opening 34 of the vessel 20 is provided for collecting the fluid to be tested. An externally threaded portion 36 of the side wall 28 is disposed adjacent to the top opening 34. The vessel 20 defines an interior 38 for collecting the fluid. In an alternative embodiment, indentations may be provided on the circumferential side wall 28 of the vessel 20 to enable convenient storage. Traction grooves may also be disposed on an outer surface of the indentations to allow for secure handling of the apparatus 10.

The apparatus 10 further comprises a carrier 50. In the preferred embodiment shown in FIGS. 1 and 3, the carrier 50 comprises a scoop 50. It is to be expressly understood, however, that the carrier 50 may comprise a variety of designs, shapes and sizes. For example, the carrier 50 may be shaped like a spoon, bucket, or any other structure capable of transporting fluid. The carrier 50 includes a receptacle 52 for retrieving and transporting at least a portion of the fluid within the vessel 20. The receptacle 52 has a bottom wall 54, a circumferential side wall 56 and a top opening 58. Thus, the bottom wall 54 and the side wall 56 define a cavity 57 in which a portion of the fluid in the vessel 20 may be disposed. The size of the receptacle 52 can be varied to vary the amount of fluid to be retrieved. A bar 60 is coupled to the receptacle 52. A removable handle 64 is coupled to the bar 60 to enable a tester to apply force to the carrier 50 in order to retrieve the fluid within the vessel. In the preferred embodiment, the handle 64 fits through an aperture 62 defined in the bar 60. A variety of handles may be employed to enable a tester to move the carrier. The carrier comprises a non-corrosive material, such as non-corrosive metal or plastic, which will not react with fluids, such as urine, or with any chemicals contained therein.

In FIGS. 1 and 2, the apparatus 10 further comprises a removable cap, or lid, 70. The cap 70 includes guide members 72 which define a passage 74 through which the bar 60 of the carrier 50 may travel. The guide members 72 define tracks 76 to enable the handle 64 of the carrier 50 to move freely. A bias mechanism 110 is disposed in the passage 74 to bias the carrier 50 towards a particular position as will be described in greater detail further below. In the preferred embodiment, the bias mechanism 110 comprises a spring 110 that pushes the carrier 50 upward. A plurality of cavities 84 are defined within the cap 70. In FIG. 1, each cavity has a near end 83 and a far end 85. An exit port 90 is disposed at the near end 83 of each cavity 84 such that the exit ports 90 are aligned and disposed within an area small enough to be covered by the area of the receptacle 52.

Figures 3, 4:
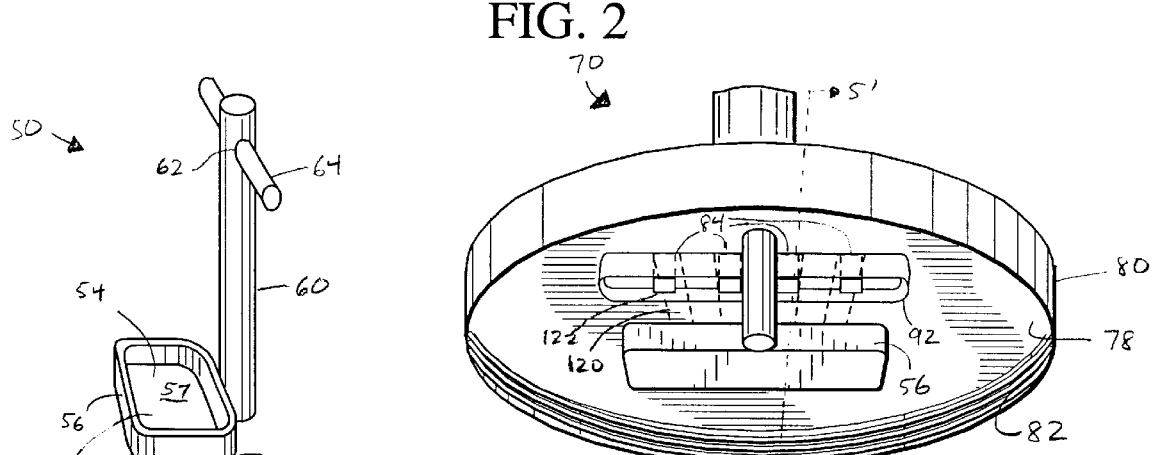
FIG. 3 is a perspective view of a carrier.
FIG. 4 is a bottom perspective view of a cap.
Figure 5:
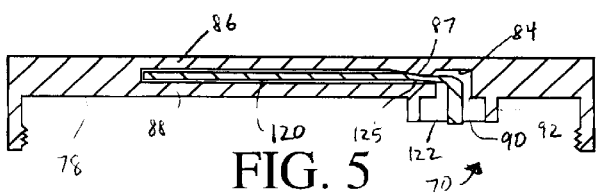
FIG. 5 is a cross-sectional view taken along lines 5'—5' of FIG. 4.

FIG. 4 is a perspective view of a bottom side 78 of the cap 70. The cap 70 includes a circumferential side wall 80 having an internally threaded portion 82 configured to mate with the externally threaded portion 36 of the vessel 20, as shown in FIG. 1. The cavities 84 are disposed in a substantially parallel array. In FIG. 5, the cavities 84 are defined within the cap 70 between an outer layer 86 and an inner layer 88. Each cavity 84 is shaped to hold a test strip 120. An end portion 122 of each test strip 120 exits through an exit port 90 defined in the inner layer 88 of the cap 70. The end portion 122 of each test strip is thus bent downward to exit through the port 90. Thus, each cavity 84 communicates with a corresponding port 90. The outer layer 86 of the cap 70 includes a downwardly protruding wedge 87 which causes pads disposed at the end 122 of the strip 120 to contact the middle portion 125 of the strip 120, such that the strip 120 functions properly. The wedge 87 also helps to push the strip 120 downward. In FIGS. 4 and 5, the cap 70 further includes a rim 92 on the bottom side 78 which surrounds the ports 90 and the protruding end portions 122 of the test strips 120. The outer perimeter of the rim 92 is configured to fit closely within the inner perimeter of the receptacle side wall 56, shown in FIG. 4, to form a sealing relationship when the receptacle 52 is brought up to contact the bottom side 78 of the cap 70. The bent ends 122 exiting the ports 90 may be separated by dividers in an alternative embodiment so as to provide separate compartments for each protruding test strip end 122. The separate compartments prevent any chemicals that may leach out from one test strip 120 from contacting the other test strips 120. This provides a more accurate test that is less vulnerable to allegations of invalidity.

Figure 6:
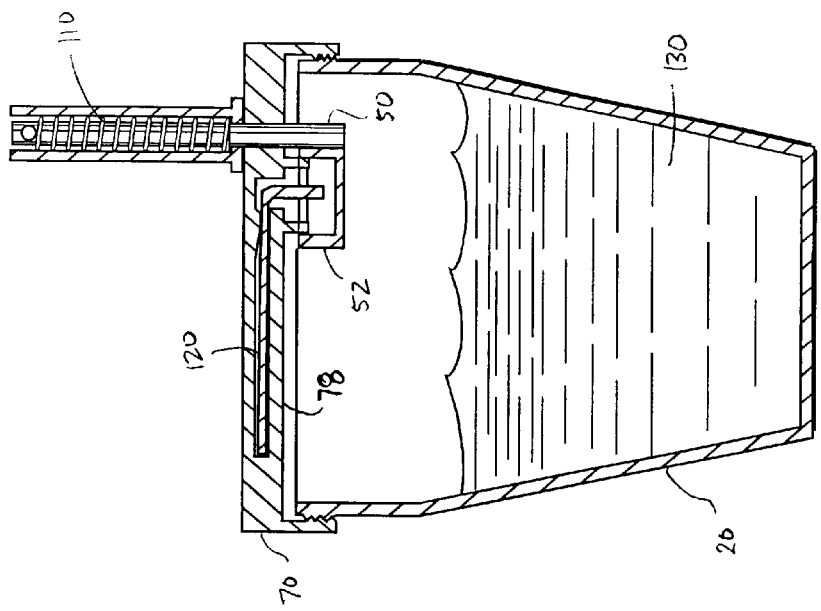
FIG. 6 is a cross-sectional view of the fluid testing apparatus in operation, showing the carrier in an initial raised position.

With the structure of the fluid testing apparatus 10 having been described, turn now to its operation. Taken along lines A'—A' of FIG. 2, FIGS. 6–8 are cross-sectional views of the apparatus 10 operating in sequence. The test strips 120, which are removed in FIG. 2, are now shown in FIGS. 6–8. Prior to securing the cap 70 to the vessel 20, however, the fluid to be tested is first disposed into the vessel 20. In the preferred embodiment, a bias mechanism 110 serves to bias the carrier 50 upward toward the closed, testing position. Therefore, in FIG. 6, the closed, testing position is the default position when no external force is applied. The receptacle 52 of the carrier 50 is disposed adjacent to the bottom surface 78 of the cap 70. In FIG. 6, the fluid 130 is collected in the vessel 20.

Figure 8:
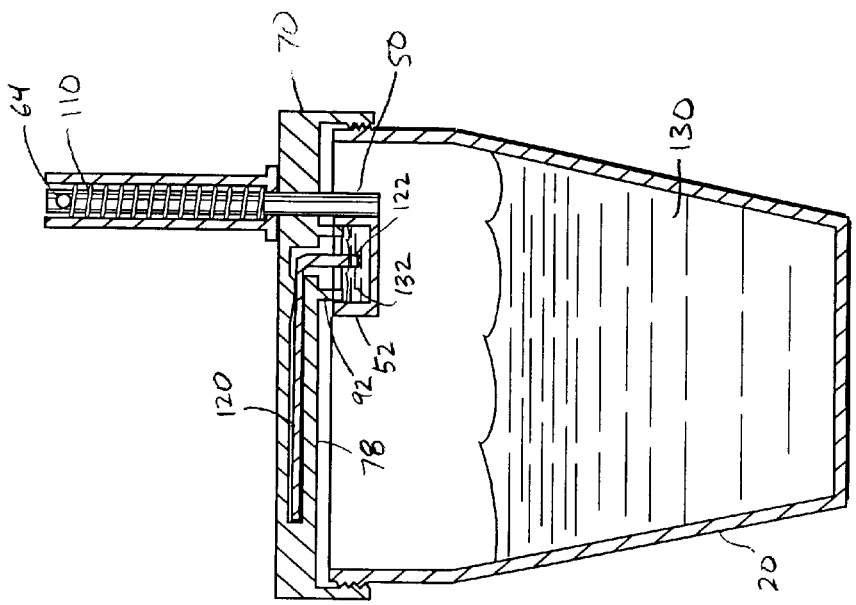
FIG. 8 is a cross-sectional view of the fluid testing apparatus in operation, showing the carrier in a final, raised position.
Figure 7:
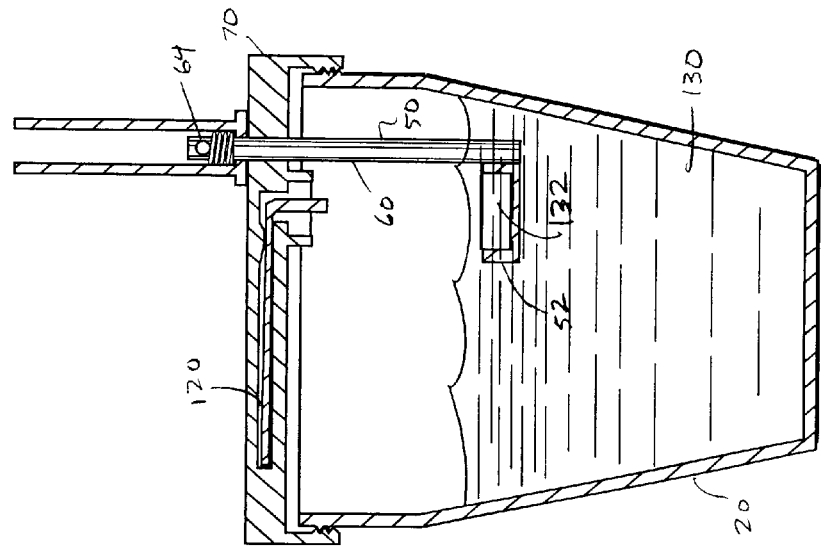
FIG. 7 is a cross-sectional view of the fluid testing apparatus in operation, showing the carrier in a lowered, retrieving position.

In FIG. 7, when the tester applies force to the carrier 50 via the handle 64, the carrier 50 is moved to a retrieving position wherein the receptacle 52 is submerged within the fluid 130 in the vessel 20. It will be appreciated that the length of the bar 60 of the carrier 50 may be varied to allow the receptacle 52 to move deeper into the vessel 20. FIG. 7 illustrates the carrier 50 in a lowered, retrieving position to collect a portion 132 of the fluid 130 in the vessel 20 with the receptacle 52. The receptacle 52 is movable between a retrieving position whereby the receptacle 52 retrieves a portion of the fluid in vessel and a testing position whereby the receptacle 52 causes the carried portion of the fluid to come into contact with a test strip 80. In the preferred embodiment, the carrier 50 is movable in vertical directions. Therefore, the retrieving, or open, position is a lowered position as shown in FIG. 7, and the testing, or closed, position is a raised position, as shown in FIGS. 6 and 8. It is to be expressly understood, however, that the carrier 50 may be movable in a variety directions and that the carrier 50 need not necessarily be limited to only vertical movement. In alternative embodiments, for instance, the carrier may be movable in horizontal directions or a combination of horizontal and vertical directions.

Since the preferred embodiment includes a spring 110 to bias the carrier 50 upward toward the closed, testing position, a tester may gently alleviate force on the handle 64 or simply release the handle 64 to allow the carrier 50 to travel upward to the testing position. In the testing position as shown in FIG. 8, the portion 132 of the fluid carried by the receptacle 52 is caused to contact the bent end portion 122 of the test strip 120. In the preferred embodiment, the test strip 120 comprises a standard chemical chromograph strip 120 having colloidal gold antibodies disposed at the near end 122 where the fluid 132 initially comes into contact. The antibodies react with either antigens disposed on the strip 120, in which case a visible band appears to indicate a negative test result, or with antigens in the fluid, in which case the absence of a band indicates a positive test result. Since the cap 70 comprises a translucent material, such as plastic, the test strips 120 may be clearly viewed from the exterior of the apparatus 10. The test strips 120 may also comprise an adulteration strip such that the cap 70 includes both drug test strips and an adulteration strip to test for drugs and contamination of the urine, respectively. This saves the technician from performing a separate adulteration test with a separate device in order to determine whether the donor purposely contaminated the urine to thwart the drug test.

In the closed position, the fluid 132 in the receptacle 52 is sealed from the remainder of the fluid 130 in the vessel 20. This is accomplished by the sealing relationship between the surrounding rim 92, the bottom surface 78 of the cap 70, and the receptacle 52. As a result, the tested fluid 132 in the receptacle 52 which has contacted the test strips 120 is prevented from leaching out and contaminating the remainder of the fluid 130 in the vessel 20. This is important should any confirmation or additional tests be desired of the remaining fluid 130.

It will be appreciated that since the closed position as illustrated in FIG. 8 is the default position by way of the spring bias mechanism 110, the entire apparatus 10 may simply be left alone once testing is done without having to perform any additional steps to prevent contamination of the remaining, non-tested fluid. Thus, the entire apparatus 10 may be sent to a different facility without any potential contamination of the non-tested fluid. A lock may be provided to keep the carrier 50 locked in the upward, testing position so as to prevent any incidental contact with the handle 64 from moving the carrier 50. It will also be appreciated that no further steps need to be taken to prevent spillage since the initial securing of the cap 70 to the vessel 20 is sufficient to keep any fluid within the vessel 20 from escaping. A gasket may be disposed along the inside diameter of the bottom surface 78 of the cap 70 to further seal the vessel and, thus, prevent any liquid from spilling out. A tester need not tilt the cup or adjust the cap to multiple, precise locations. The simplicity of the fluid testing apparatus 10 enables a tester to perform a test by simply pressing down and letting go. Thus, the apparatus 10 eliminates the plurality of steps involved in prior art devices.

Many alterations and modifications may be made by those having ordinary skill in the art without departing from the spirit and scope of the invention. Therefore, it must be understood that the illustrated embodiments have been set forth only for the purposes of example and that it should not be taken as limiting the invention as defined by the following claims. The claims are thus to be understood to include what is specifically illustrated and described above, what is conceptionally equivalent, what can be obviously substituted and also what essentially incorporates the essential idea of the invention.

What is claimed is:

1. A fluid testing apparatus comprising:
   a container for containing a fluid; the container comprising a cap;
   a test strip disposed within the cap; and
   a movable carrier to carry at least a portion of the fluid, the movable carrier being movable between a retrieving position where the carrier retrieves the portion of the fluid within the container and a testing position where the carrier causes the portion of the fluid to come into contact with at least a portion of the test strip.

2. The apparatus of claim 1 wherein the container further comprises a vessel.

3. The apparatus of claim 2 wherein the test strip is disposed at least in part within a cavity in the cap.

4. The apparatus of claim 3 wherein the cap comprises a translucent material such that the test strip disposed within the cavity is viewable.

5. The apparatus of claim 3 wherein the test strip comprises an end portion that projects downwardly from the cap so as to be accessible for contact with the fluid carried by the movable carrier.

6. The apparatus of claim 5 wherein the cap further comprises a rim on a bottom side that surrounds the end portion of the test strip, the rim being adapted to form a sealing relationship with the movable carrier when the movable carrier is in a first position.

7. The apparatus of claim 2 wherein the cap is removably secured to the vessel.

8. The apparatus of claim 2 wherein the movable carrier comprises a receptacle coupled to a bar.

9. The apparatus of claim 8 wherein the receptacle is disposed beneath the cap and within the vessel.

10. The apparatus of claim 9 wherein the bar extends through the cap.

11. The apparatus of claim 10 further comprising a bias mechanism to bias the receptacle in a direction toward the test strip.

12. A fluid testing apparatus comprising:
    a vessel to collect a fluid;
    a lid coupled to the vessel;
    a test strip disposed at least in part within the lid; and
    a movable carrier having a receptacle disposed within the vessel to carry a portion of the fluid, wherein the movable carrier is movable between a retrieving position where the receptacle retrieves the portion of the fluid within the vessel and a testing position where the receptacle causes the portion of the fluid to come into contact with at least a portion of the test strip.

13. The apparatus of claim 12 wherein the movable carrier forms a sealing relationship with the lid in the testing position.

14. The apparatus of claim 12 wherein the testing position is an upper position and the retrieving position is a lower position.

15. The apparatus of claim 12 further comprising a bias mechanism to bias the movable carrier toward the testing position.

16. The apparatus of claim 12 wherein the lid is removable.

17. The apparatus of claim 12 wherein the test strip comprises a drug test strip.

18. The apparatus of claim 17 further comprising an adulteration strip disposed at least in part within the lid.

* * * * *